US012409343B2

United States Patent
Liou (10) Patent No.: US 12,409,343 B2
(45) Date of Patent: Sep. 9, 2025

(54) BIOLOGICAL OBJECT IMAGE-CAPTURING AND TREATMENT SYSTEM AND METHOD

(71) Applicant: Taipei Medical University, Taipei (TW)

(72) Inventor: Jian-Chiun Liou, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 304 days.

(21) Appl. No.: 17/729,578

(22) Filed: Apr. 26, 2022

(65) Prior Publication Data

US 2022/0257983 A1    Aug. 18, 2022

Related U.S. Application Data

(63) Continuation-in-part of application No. 16/902,300, filed on Jun. 16, 2020, now Pat. No. 11,351,400.

(30) Foreign Application Priority Data

Sep. 16, 2019   (TW) .................................. 108133280

(51) Int. Cl.
*A61N 7/00*          (2006.01)
(52) U.S. Cl.
CPC ........ *A61N 7/00* (2013.01); *A61N 2007/0052* (2013.01)
(58) Field of Classification Search
CPC ................ A61N 2007/0052; A61N 2007/0078
See application file for complete search history.

(56) References Cited

U.S. PATENT DOCUMENTS

| 6,736,779 B1* | 5/2004 | Sano ........................ A61B 8/14 600/447 |
|---|---|---|
| 2004/0015079 A1 | 1/2004 | Berger et al. |
| 2018/0104500 A1* | 4/2018 | Blum ................. A61N 1/36125 |
| 2020/0353292 A1* | 11/2020 | Hunt ........................ A61N 7/02 |
| 2021/0016113 A1* | 1/2021 | Hunt ........................ A61N 7/00 |

(Continued)

FOREIGN PATENT DOCUMENTS

| CN | 1112903 C | 7/2003 |
|---|---|---|
| CN | 101972154 A | 2/2011 |

(Continued)

*Primary Examiner* — Joel Lamprecht
*Assistant Examiner* — Nyrobi Celestine
(74) *Attorney, Agent, or Firm* — BACON & THOMAS, PLLC (57) ABSTRACT

A biological object image-capturing and treatment system includes a micro detection and treatment device, and an AI model. The micro detection and treatment device includes a plurality of signal transmitting and receiving elements, wherein one of the signal transmitting and receiving elements continuously transmits a stimulation signal with different parameter values to a particular target, and one of the signal transmitting and receiving elements continuously receives response signal from the particular target. The AI model uses the response signals to perform machine learning, and outputs a parameter value adjustment suggestion to the micro detection and treatment device according to result of the machine learning. The micro detection and treatment device adjusts the parameter value of the stimulation signal according to the parameter value adjustment suggestion.

8 Claims, 7 Drawing Sheets

(56) References Cited

U.S. PATENT DOCUMENTS

2021/0138276 A9* 5/2021 Kabrams ................ A61B 5/291
2021/0196233 A1* 7/2021 Levy ....................... A61N 7/02

FOREIGN PATENT DOCUMENTS

| CN | 105310726 A | 2/2016 |
| CN | 205306997 U | 6/2016 |
| CN | 106650201 A | 5/2017 |

* cited by examiner

BIOLOGICAL OBJECT IMAGE-CAPTURING AND TREATMENT SYSTEM AND METHOD

CROSS REFERENCE TO RELATED APPLICATION

This application claims the benefits of the Taiwanese Patent Application Serial Number 108133280, filed on Sep. 16, 2019, the subject matter of which is incorporated herein by reference.

This application is a continuation in part (CIP) of U.S. patent application for "Biological object image-capturing and treatment system and method", U.S. application Ser. No. 16/902,300 filed Jun. 16, 2020, and the subject matter of which is incorporated herein by reference.

BACKGROUND OF THE INVENTION

1. Field of the Invention

The present invention relates to a biological object image-capturing and treatment system with low noise and a method thereof.

2. Description of Related Art

Radiological medicine technology has been widely used in medical treatment behavior, such as ultrasound image-capturing technology or ultrasound therapy technology. Ultrasonic technology is provided with the following advantages: (1) it is less radioactive and therefore less harmful to the human body in comparison with other technologies; (2) its price is lower than other inspection techniques; (3) its equipment volume is smaller, and thus more flexible; and (4) the image-capturing speed is fast and the resolution is high. However, ultrasonic probes typically use piezoelectric transducers as signal transmitting and receiving components, and the materials of these transducers include piezoelectric polycrystalline ceramic materials, wherein the silver surface plated on the ceramic materials is connected to the electrode of the next transducer. Therefore, these ceramic materials are likely to produce resonance and, when adjacent transducers transmit or receive signals, the problem of signal interference often occurs.

In addition, there is currently no ultrasonic device into which the image-capturing function and the treatment function are integrated, and thus there are still deficiencies in terms of space occupation, production cost, or usage convenience.

In addition, different biological objects or different positions may have different absorption degrees for ultrasonic signal, so that how to select ultrasonic signal with an appropriate power level for different biological objects or different positions becomes a problem that needs to be solved. So far, this problem can be solved only by manual adjustment, and the efficiency is very low.

Therefore, it is desirable to provide an improved biological object image-capturing and treatment system and method to mitigate and/or obviate the aforementioned problems.

SUMMARY OF THE INVENTION

The object of the present invention is to provide a biological object image-capturing and treatment system and method, with which not only the image-capturing function, the treatment function and the stimulation function are integrated into the same device for reducing the occupied space of the device, but also special signal transmitting operation modes are employed to greatly reduce the interference between transmitting and receiving elements of each signal in the device, thereby significantly improving the signal accuracy. Besides, the biological object image-capturing and treatment system is integrated with an artificial intelligence model for automatically adjusting the parameter values of the ultrasonic signal transmitted from the biological object image-capturing and treatment system.

In one aspect of the present invention, there is provided a biological object image-capturing and treatment system for performing an object stimulation procedure. The system comprises a micro detection and treatment device including a plurality of signal transmitting and receiving elements and an AI model. One of the signal transmitting and receiving elements continuously transmits a stimulation signal with different parameter values to a particular target, and one of the signal transmitting and receiving elements continuously receives response signal corresponding to the stimulation signal with different parameter values from the particular target. The AI model uses the response signals corresponding to the stimulation signal with different parameter values from the particular target to perform a machine learning, and outputs a parameter value adjustment suggestion to the micro detection and treatment device according to result of the machine learning. The micro detection and treatment device adjusts the parameter value of the stimulation signal according to the parameter value adjustment suggestion.

In another aspect of the present invention, there is provided a biological object image-capturing and treatment method performed by a biological object image-capturing and treatment system. The biological object image-capturing and treatment system comprises a micro detection and treatment device including a plurality of signal transmitting and receiving elements and an AI model. The method includes the steps of: continuously transmitting a stimulation signal with different parameter values to a particular target by one of the signal transmitting and receiving elements; continuously receiving response signal corresponding to the stimulation signal with different parameter values from the particular target by one of the signal transmitting and receiving elements; using the response signals corresponding to the stimulation signal with different parameter values to perform a machine learning by the AI model, and outputting a parameter value adjustment suggestion according to result of the machine learning to the micro detection and treatment device by the AI model; and adjusting the parameter value of the stimulation signal according to the parameter value adjustment suggestion by the micro detection and treatment device.

Other objects, advantages, and novel features of the invention will become more apparent from the following detailed description when taken in conjunction with the accompanying drawings.

DETAILED DESCRIPTION OF THE PREFERRED EMBODIMENT

The implementations of the present disclosure will be described with specific embodiments in the following description. A person skilled in the art will understand the advantages and the effects provided by the present disclosure. Different specific embodiments may be applicable according to the present disclosure.

Moreover, the orders such as "first", "second", and so on, in the specification and the claims are only used to distinguish the elements with the same name. They do not have their own specific meanings, do not necessarily mean that there is another element existing in addition to one element, and do not mean that there is a priority between one element and another element, or one step and another step.

Besides, in the present disclosure, the description such as "A happens when B happens" may refer to A happens before, when or after B happens, and it does not necessarily refer to A and B happen at the same time, except that a clear limitation is given. In the present disclosure, the description such as "A is disposed on B" refers to the corresponding locations of A and B, and it does not necessarily refer to the contact of A and B, except that a clear limitation is given. Moreover, the word "or" between the elements or their effects in the present disclosure means that the elements and the effects may exist individually or together.

In addition, in the present invention, the terms such as "connected", "electrically connected" or "coupled", unless otherwise emphasized, mean that the direct connection and the indirect connection are included. In addition, the terms "including", "including", "having", and "having" in this disclosure are all open descriptions, which are described first.

Furthermore, various embodiments of the biological object image-capturing and treatment system 1 of the present invention can be realized by a software program or an electronic circuit, and are not limited thereto.

Figure 1:
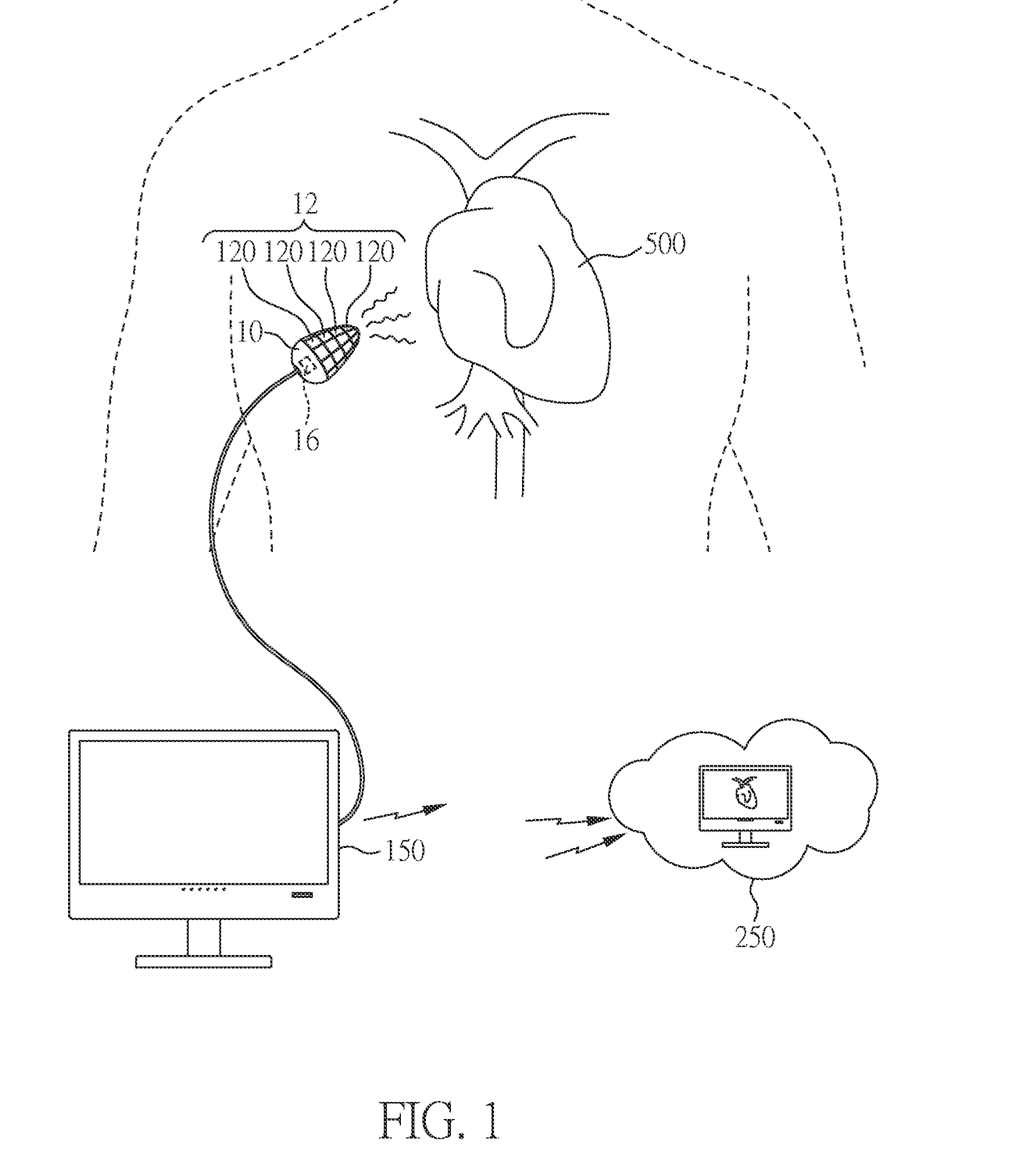
FIG. 1 is a schematic diagram illustrating the biological object image-capturing and treatment system according to an embodiment of the present invention.

FIG. 1 is a schematic diagram illustrating the biological object image-capturing and treatment system according to an embodiment of the present invention, wherein the biological object image-capturing and treatment system 1 may be used to perform an image-capturing procedure, a treatment procedure or an object stimulation procedure. As shown in FIG. 1, the biological object image-capturing and treatment system 1 at least includes one micro detection and treatment device 10. Further, the biological object image-capturing and treatment system 1 may further include a user operating device 150 and a cloud server 250. The micro detection and treatment device 10 includes a signal transmitting and receiving element array 12, and the signal transmitting and receiving element array 12 includes a plurality of signal transmitting and receiving elements 120, wherein the plurality of signal transmitting and receiving elements 120 can be arranged in an array, but it is not limited thereto. The signal transmitting and receiving elements 120 are configured in such a manner that: the adjacent at least two signal transmitting and receiving elements 120 respectively transmit signals or receive signals during different periods; that is, the period during which one signal transmitting and receiving element 120 transmits or receives signals does not overlap the period during which another signal transmitting and receiving element 120 transmits or receives signals. It should be noted that the "period" herein may be in a state of continuous time or instantaneous time. In addition, the micro detection and treatment device 10 may also include a controller 16 for controlling the operation of the micro detection and treatment device 10. In one embodiment, the micro detection and treatment device 10, the user operating device 150 and the cloud server 250 may transmit data to each other. The image-capturing procedure and the treatment procedure may be handled by separate subsystems, or the image-capturing procedure and the treatment procedure may be handled by a common system.

The micro detection and treatment device 10 is a medical detecting device, and has both an image-capturing function and a treatment function, wherein "micro" is defined as a size capable of being inserted into a human body. However, the micro detection and treatment device 10 can also be used outside the human body. In one preferred embodiment, the micro detection and treatment device 10 is an ultrasonic detection and treatment device, and thus the signal transmitting and receiving element 120 is used for transmitting and receiving ultrasonic signals, but is not limited thereto. For convenience of description, the following description is given by taking the transmitting and receiving elements to transmit or receive ultrasonic signals as an example. When the biological object image-capturing and treatment system 1 performs an image-capturing process, the micro detection and treatment device 10 may transmit a first power signal to different positions of a target object 500 through the signal transmitting and receiving elements 120, and may receive signals reflected from different positions of the target object 500 through the signal transmitting and receiving elements 120. Furthermore, the reflected signals may be integrated through the user operating device 150 or the cloud server 250 so as to combine an ultrasonic image of the target object 500. When the biological object image-capturing and treatment system 1 performs a treatment procedure, the micro detection and treatment device 10 may transmit a second power signal to a specific position of the target object 500 through the signal transmitting and receiving elements 120, thereby treating the specific position of the target object 500, for example, ablation and other treatment behaviors. It should be noted that the first power signal and the second power signal have different powers or different frequencies. In one embodiment, the power of the first power signal is less than the power of the second power signal. In one embodiment, the frequency of the first power signal is higher than the frequency of the second power signal. As a result, the first power signal is suitable for object image-capturing, and the second power signal is suitable for treatment behavior such as ablation. Besides, when the object stimulation procedure is performed, the signal transmitting and receiving elements 120 can transmit stimulation signal to an object, wherein each of the signal transmitting and receiving elements 120 corresponds to different object or different position of the same object. The stimulation signal can be ultrasonic signal. In one embodiment, the power of the stimulation signal is smaller than that of the first power signal and the second power signal, but it is not limited thereto.

In addition, the micro detection and treatment device 10 may be, for example, an invasive medical device, so that it has a smaller volume than the existing handheld ultrasonic device. In FIG. 1A, the target object 500 is exemplified by the heart of a human body, and the micro detection and treatment device 10 may be placed near the heart to perform image-capturing and treatment on the heart vascular wall, vein, and the like. In one embodiment, the micro detection and treatment device 10 may be of medical grade material suitable for placement into a human body. In one embodiment, at least a portion of the micro detection and treatment device 10 is a disposable component and can be replaced.

In one embodiment, the diameter of each of the signal transmitting and receiving elements 120 is equal to or smaller than 10000 micrometers (μm). In one embodiment, the diameter of each of the signal transmitting and receiving elements 120 is in a range of 4000 μm to 6000 μm (i.e. 4000 μm≤diameter≤6000 μm). In one embodiment, the diameter of each of the signal transmitting and receiving elements 120 is substantially 5000 μm. However, the invention is not limited thereto.

Since the micro detection and treatment device 10 of the invention can be inserted into the human body, compared to the prior technique, the micro detection and treatment device 10 is closer to a treatment target. Furthermore, because of having small volume, the signal transmitting and receiving elements 120 can provide more precise and accurate imaging distance, imaging depth and imaging width, so as to make a reflection of dose-response relationship more accurate.

Besides, since the micro detection and treatment device 10 may perform an image-capturing procedure and a treatment procedure, the present invention may further perform steps to achieve treatment and resection of the proliferative tissue at a specific position in the human body.

Please refer to FIG. 1 again. The user operating device 150 may be connected to the micro detection and treatment device 10 in a manner of wired transmission or wireless transmission, whereby the user may transmit a control command to the micro detection and treatment device 10 through the user operating device 150. In one embodiment, the user operating device 150 may be various electronic devices with a microprocessor, such as a desktop computer, a notebook computer, a smart phone, a tablet computer, a touch device, and the like, and is not limited thereto. More details regarding the user operating device 150 will be explained in more detail in the subsequent paragraphs with reference to FIG. 3(B).

The cloud server 250 may perform data backup or data processing. In one embodiment, after the signal transmitting and receiving elements 120 receive the reflected signal from the target object 500, instead of performing image formation, the micro detection and treatment device 10 transfers the data to the user operating device 150 or the cloud server 250 to perform image formation. In one embodiment, an AI model for performing machine learning can be disposed on the cloud server 250, but it is not limited thereto.

Figure 2:
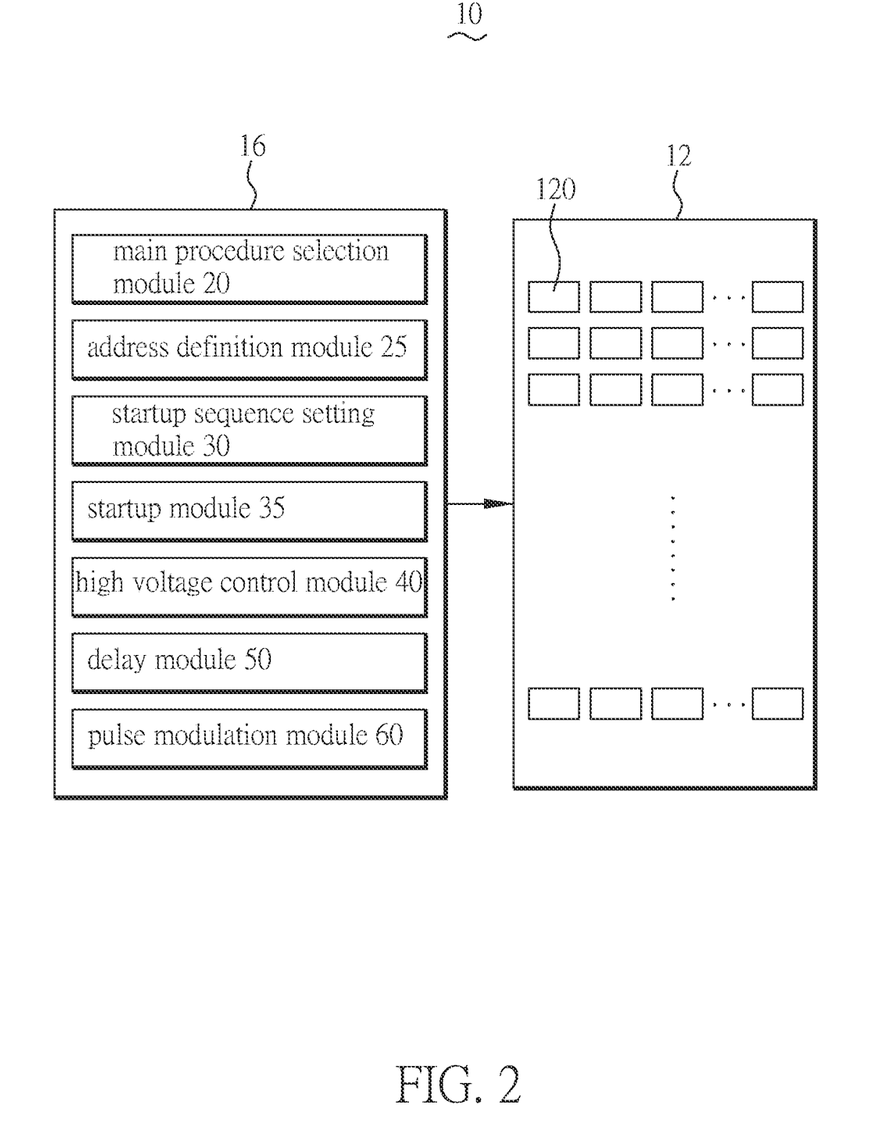
FIG. 2 schematically illustrates a controller of a micro detection and treatment device according to an embodiment of the present invention.

Next, the detailed structure of the controller 16 of the micro detection and treatment device 10 will be described.

FIG. 2 schematically illustrates a controller 16 of a micro detection and treatment device 10 according to an embodiment of the present invention. With reference to both FIG. 1(A) and FIG. 2, the controller 16 is disposed inside the micro detection and treatment device 10. The controller 16 may be coupled to the signal transmitting and receiving element array 12 to control the operation of the signal transmitting and receiving elements 120. In one embodiment, the controller 16 may include a main procedure selection module 20, an address definition module 25, a startup sequence setting module 30, and a startup module 35. Alternatively, the micro detection and treatment device 10 may further include a high voltage control module 40, a delay module 50, and a pulse modulation module 60. The type and the quantity of the aforementioned modules are only examples and are not limited, and may be arbitrarily increased or decreased according to the needs of the user. In addition, the modules may be arbitrarily connected or integrated as long as they can be realized. In one embodiment, the controller 16 is a control chip, and the function of each module can be implemented by at least one digit logic circuit or computer program, and is not limited thereto.

First, the main procedure selection module 20 is described. The main procedure selection module 20 may be used to execute an image-capturing procedure, a treatment procedure or an object stimulation procedure. For example, the main procedure selection module 20 selects the image-capturing procedure or the treatment procedure for execution according to a predetermined command or a control command of the user operating device 150, and further controls the signal transmitting and receiving element array 12 to transmit the first power signal or the second power signal. In addition, in one embodiment, the main procedure selection module 20 may further select different image-capturing modes for execution. For example, the image-capturing procedure may include a first image-capturing mode, a second image-capturing mode, a third image-capturing mode and a fourth image-capturing mode, and the treatment procedure may include a first treatment mode and a second treatment mode, which will be described in order in the following.

In one embodiment, the first image capturing mode is set to transmit the first power signal to different positions of the target object 500 by using a single signal transmitting and receiving element 120, and receive reflection signals reflected from the different positions of the target object 500 at different time points by using a single signal transmitting and receiving element 120. In this embodiment, the signal transmitting and receiving element that transmits the first power signal is not limited to be the same as the signal transmitting and receiving element that receives the reflection signals. In addition, since a single signal transmitting and receiving element 120 must transmit signals toward different positions of the target object 500, the signal transmitting and receiving element array 12 is designed to be rotatable, but is not limited thereto.

In one embodiment, the second image-capturing mode is set to transmit the first power signal to different positions of the target object 500 by using a plurality of signal transmitting and receiving elements 120, and receive reflection signals reflected from the different positions of the target object 500 at different time points by using a single signal transmitting and receiving element 120. In this embodiment, between the signal transmitting and receiving elements 120 that transmit signals, there is an interval of at least one signal transmitting and receiving element, and thus they are not adjacent to each other. In addition, signals may be transmitted simultaneously or sequentially. In addition, the signal transmitting and receiving elements 120 that transmit signals may also be used to receive signals.

In one embodiment, the third image-capturing mode is set to transmit the first power signal to different positions of the target object 500 by using a single signal transmitting and receiving element 120, and receive reflection signals reflected from the different positions of the target object 500 at different time points by using a plurality of signal transmitting and receiving elements 120. Between the signal transmitting and receiving elements 120 that receive signals, there is an interval of at least one signal transmitting and receiving element, and thus they are not adjacent to each other. In addition, the signal transmitting and receiving element 120 that transmits signals may also be used to receive signals.

In one embodiment, the fourth image-capturing mode is set to transmit the first power signal to different positions of the target object 500 by using a plurality of single signal transmitting and receiving elements 120, and receive reflection signals reflected from the different positions of the target object 500 at different time points by using a plurality of signal transmitting and receiving elements 120. In this embodiment, the signal transmitting and receiving elements 120 that transmit signals are not adjacent to each other, and the signal transmitting and receiving elements 120 that receive signals are also not adjacent to each other. In this embodiment, the signal transmitting and receiving elements 120 that transmit signals may not be in consistency with the signal transmitting and receiving elements 120 that receive signals. In addition, signals can be transmitted simultaneously or sequentially.

In one embodiment, the first treatment mode is set to transmit the second power signal to different positions of the target object 500 by using a single signal transmitting and receiving element 120. It is noted that, when the first treatment mode is executed, the second power signal from the single signal transmitting and receiving element 120 does not need to be focused.

In one embodiment, the second treatment mode is set to transmit the second power signal to the different positions of the target object 500 by using a plurality of signal transmitting and receiving elements 120. In this embodiment, the signal transmitting and receiving elements 120 that transmit signals are not adjacent to each other. In addition, signals can be transmitted simultaneously or sequentially. It is noted that, when the second treatment mode is executed, the second power signal from the single signal transmitting and receiving elements 120 do not need to be focused.

Next, the address definition module 25 is described. The address definition module 25 may define the address parameter of each signal transmitting and receiving element 120. For example, if the signal transmitting and receiving element array 12 has 64 signal transmitting and receiving elements 120, there are also 64 address parameters, and each signal transmitting and receiving element 120 corresponds to one address parameter.

Next, the startup sequence setting module 30 is described. When using a plurality of signal transmitting and receiving elements 120 to transmit or receive signals, in order to avoid interference generated between the adjacent signal transmitting and receiving elements in operation, the startup sequence setting module 30 may control the signal transmitting and receiving elements 120 to perform a specific startup sequence mode so as to shift the transmitting and receiving timing of the adjacent signal transmitting and receiving elements 120. The specific startup sequence mode is provided to sequentially or simultaneously start the signal transmitting and receiving elements in a manner of spacing N signal transmitting and receiving elements 120, wherein N is a positive integer of 1 or more (1≤N), and N is smaller than the total number of the signal transmitting and receiving elements 120.

In one embodiment, the startup sequence setting module 30 may execute a first startup sequence mode, wherein the signal transmitting and receiving elements 120 are sequentially or simultaneously started in a manner of spacing one signal transmitting and receiving element 120. Under this startup sequence, the signal transmitting and receiving elements of odd address parameter are started sequentially or simultaneously to receive or transmit signals. When the signal transmitting and receiving elements of odd address parameter complete the signal receiving or transmitting, the signal transmitting and receiving elements of even address parameter will start receiving or transmitting signals sequentially or simultaneously. In addition, it is also possible to first start the operation by using the signal transmitting and receiving element of even address parameter.

On this basis, there N types of startup sequence modes are available for execution to prevent adjacent 1 to N signal transmitting and receiving elements 120 from performing signal transmitting or receiving during the same period, thereby avoiding interference problem among the ultrasonic signals. The N types of startup sequence modes may be suitable for signal transmitting or receiving in the image-capturing procedure or the treatment procedure.

Next, the startup module 35 is described. The startup module 35 may generate a plurality of startup signals according to the startup sequence mode set by the startup sequence setting module 30, wherein the startup signals correspond to the address parameters corresponding to the startup sequence mode, and are used to actually start the signal transmitting and receiving elements 120 corresponding to the address parameters. For example, when the second startup sequence mode is set, the startup module 35 transmits the startup signal to the signal transmitting and receiving elements 120 corresponding to the address parameters according to the startup sequence of the second startup sequence mode (for example, first starting the address parameters of 1, 4, 7, 10 and so on, and then starting the address parameters of 2, 5, 8, 11 and so on), so as to start the signal transmitting and receiving elements 120 for performing signal transmitting or receiving.

Next, the high voltage control module 40 is described. In one embodiment, since the voltage required for the signal transmitting and receiving elements 120 to transmit the ultrasonic signals is as high as 40 volts (40 V) or more, a high voltage must be applied to drive the signal transmitting and receiving elements 120 through the high voltage control module 40, and thus the high voltage control module 40 can be used to control whether the signal transmitting and receiving elements 120 actually transmit the ultrasonic signals. With this feature, the high voltage control module 40 may also be used to assist in avoiding interference caused by adjacent at least two signal transmitting and receiving elements. For example, the high voltage control module 40 may detect whether the adjacent at least two signal transmitting and receiving elements 120 receive the startup signal at the same time or in a specific time. If yes, the high voltage control module 40 may output a disable signal (for example, "0") for the at least two signal transmitting and receiving elements 120; that is, no high voltage is applied to the at least two signal transmitting and receiving elements 120. If not, the high voltage control module 40 may output an enable signal (for example, "1") for the at least two signal transmitting and receiving elements 120; that is, a high voltage is applied to the at least two signal transmitting and receiving elements 120. However, the invention is not limited thereto. In one embodiment, the high voltage control module 40 is a hardware circuit; while the invention is not limited thereto.

Next, the delay module 50 is described. In one embodiment, the delay module 50 may control the signal transmitting periods of the adjacent at least two signal transmitting and receiving elements 120 to have a time interval ($\Delta T$) in advance, so that the adjacent two signal transmitting and receiving elements 120 will not perform signal transmitting and receiving during the same period regardless of the startup sequence mode.

Next, the pulse modulation module 60 is described. In one embodiment, because the fault of the controller 16 caused by certain factors during the manufacturing process may result in the micro detection and treatment device 10 failing to output the correct power, the first power signal or the second power signal may be affected, resulting in a negative influence to the image-capturing or treatment quality. Therefore, the controller 16 may be configured with a pulse modulation module 60 for performing pulse width modulation on the signals inputted to the controller 16 or the signals outputted from the controller 16 so as to correct and enhance the signals, thereby allowing the micro detection and treatment device 10 to output the power of stable ultrasonic signal. However, the invention is not limited thereto.

Figure 3A:
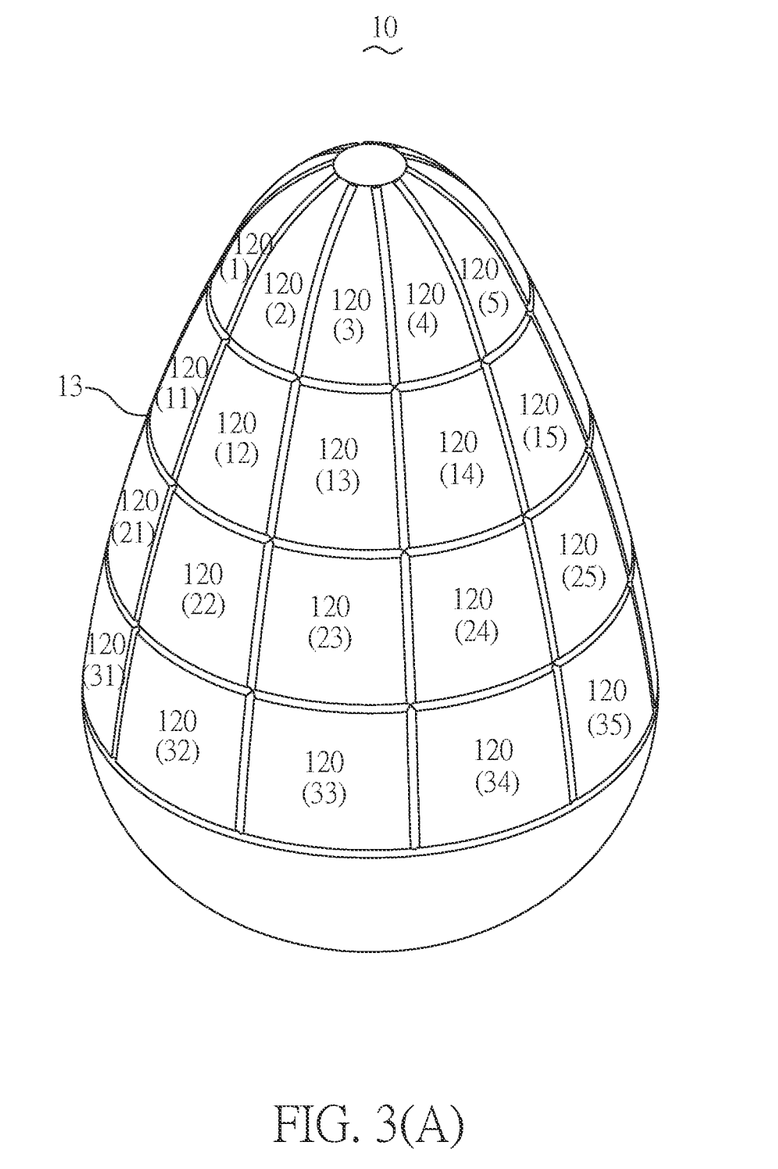
FIG. 3(A) schematically illustrates a signal transmitting and receiving element array according to an embodiment of the present invention.

Next, the detailed features of the signal transmitting and receiving element array 12 are described. FIG. 3(A) schematically illustrates a signal transmitting and receiving element array according to an embodiment of the present invention. As shown in FIG. 3(A), the micro detection and treatment device 10 may have a cylindrical probe portion 13, and the signal transmitting and receiving element array 12 surrounds the probe portion 13 by, for example, 360 degrees. In one example, the signal transmitting and receiving element array 12 may be provided with 64 signal transmitting and receiving elements 120, which are equally arranged into an array and are divided into 4 rows, each row having 16 elements, each element being assigned with an address parameter (shown as brackets and numbers in the figure), but are not limited thereto. In other embodiments, the signal transmitting and receiving element array 12 may also be provided with other quantity of signal transmitting and receiving elements 120, such as 16, 32, 128 or 256. In one embodiment, the signal transmitting and receiving element array 12 and the probe portion 13 may be provided with a pivoting mechanism. Therefore, the signal transmitting and receiving element array 12 is rotatable relative to the probe portion 13, but is not limited thereto. In one embodiment, the material of the signal transmitting and receiving element 120 is PZT (lead-zirconate-titanate), but is not limited thereto. In addition, in one embodiment, intervals may be provided between different rows, and thus each row may be regarded as a ring, but is not limited.

Figure 3B:
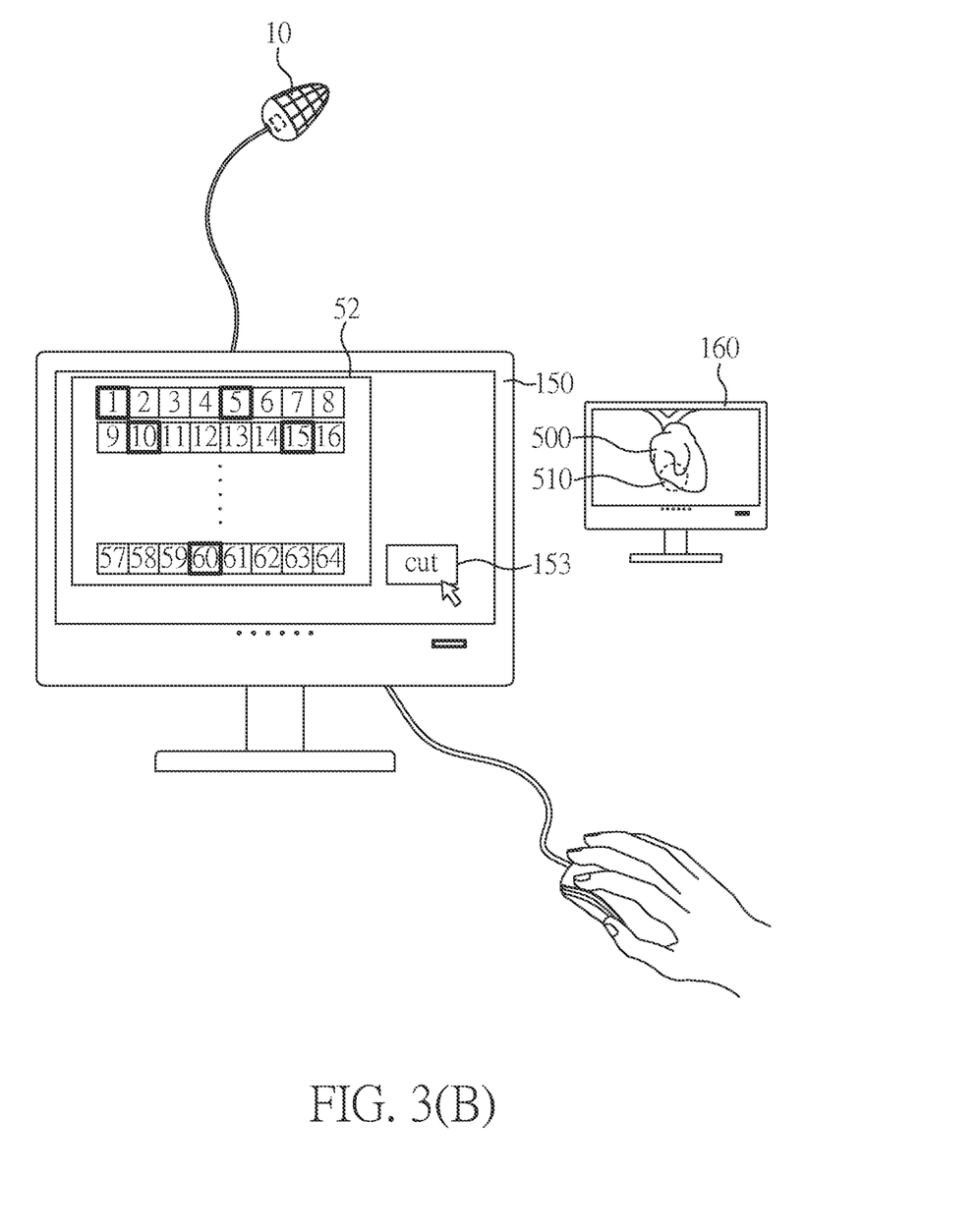
FIG. 3(B) schematically illustrates a user operating device corresponding to the signal transmitting and receiving element array according to an embodiment of the present invention.

FIG. 3(B) schematically illustrates a user operating device corresponding to the signal transmitting and receiving element array 12 according to an embodiment of the present invention. With reference to FIG. 3(B) and FIGS. 1(A) to 3(A), in one embodiment, the image (target object 500 and treatment portion 510) obtained by the image-capturing procedure may be displayed on a display device 160, and the address parameter of each signal transmitting and receiving element 120 may correspond to a lookup table. The user operating device 150 may be provided with a display area 52 for correspondingly displaying each address parameter according to the lookup table, and presenting each address parameter in a form of user-selectable key. Therefore, the user may directly select the desired signal transmitting and receiving element 120 on the user operating device 150 according to the treatment portion 510 of the target object 500 and, after the selection, uses a startup button 153 on the user operating device 150 to transmit a control command to the micro detection and treatment device 10. In addition, in another embodiment, the display device 160 can be integrated into the user operating device 150; that is, the image obtained by the image-capturing procedure can be displayed in the display area 52 at the same time with the address parameter of each signal transmitting and receiving element 120. However, the present invention is not limited thereto.

In one embodiment, when the micro detection and treatment device 10 transmits the "treatment signal (e.g. the second power signal)", the display device 160 simultaneously displays the image-capturing of the treatment target, and the change of the treatment target can be presented. Thus, various treatment parameters (e.g. the treatment signal power, treatment period, etc.) can be adjusted in real time. In addition, since the display device 160 can display image-capturing in real time during the treatment process, the user or the micro detection and treatment device 10 can obtain the actual treatment area through the ratio conversion of the ultrasound image (e.g. correlation coefficient), and then determine whether to adjust the treatment position. In one embodiment, "simultaneously displaying the ultrasound images" can be achieved at least by: using the energy reflected from the treatment location to execute the piezo-electricity image-capturing on the same axis space of the treatment location.

In one embodiment, since the display device 160 can display images in real time during the treatment process, the biological object image-capturing and treatment system 1 of the present invention can provide a function of monitoring the treatment process. In addition, since the monitoring function can be performed before or during the treatment process, the accuracy of the treatment can be improved.

The user operating device 150 may have various implementations, for example, the user operating device 150 can be integrated with the micro detection and treatment device 10 or the user operating device 150 has a handle, but it is not limited thereto.

Figure 4:
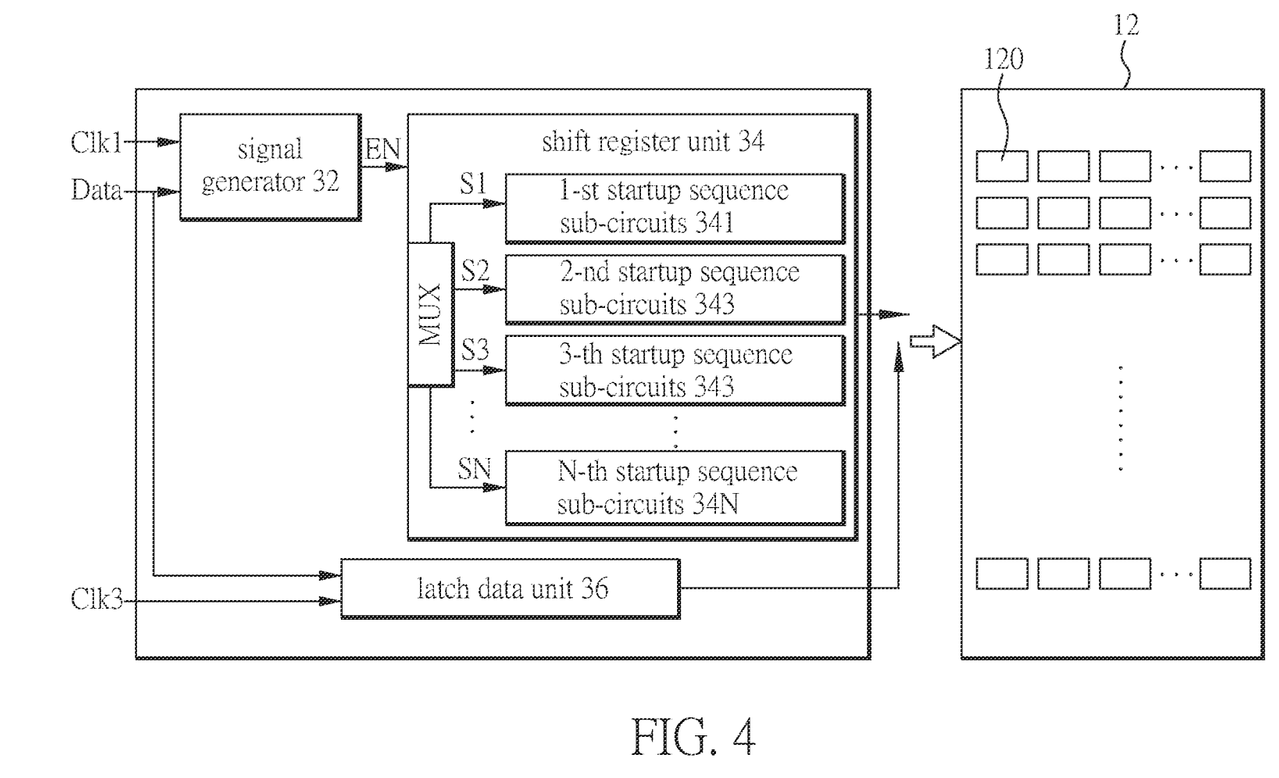
FIG. 4 is a circuit diagram of a mode control module and a startup module according to an embodiment of the invention.

The functions of the startup sequence setting module 30 and the startup module 35 of the present invention may be implemented by a digital logic circuit, which is described by way of an example in the following, but the invention is not limited to the example. FIG. 4 is a circuit diagram of the mode control module 30 and the startup module 35 according to an embodiment of the invention, and please refer to FIG. 1 to FIG. 3(B) at the same time.

As shown in FIG. 4, the detailed structure of the mode control module 30 and the startup module 35 may include a signal generator 32, a shift register unit 34, and a latch data unit 36. The shift register module 34 is coupled to the signal generator 32, and includes 1-st to N-th startup sequence sub-circuits 341-34N, wherein each of the startup sequence sub-circuits 341-34N corresponds to a startup sequence mode. The latch data unit 36 outputs a latch signal, and the latch signal is latched with the output of each of the startup sequence sub-circuits 341-34N.

In one embodiment, the signal generator 32 receives a first clock signal (Clk1) and a data signal (Data), and generates a second clock signal (hereinafter referred to as an enable signal (EN)) according to a first clock signal (Clk1) and the data signal (Data). The shift register module 34 receives the enable signal, and multiplexes and shifts the data signal (Data) according to the enable signal (EN), thereby generating N address signals (S1~SN), wherein each of the address signals (S1~SN) controls the output signal (i.e., startup signal) of one of the startup sequence sub-circuits 341-34N, thereby controlling whether the startup sequence mode is ready to start. The latch data unit 36 performs an AND operation on the output signals (i.e., start signals) of the startup sequence sub-circuits 341-34N according to the data signal (Data) and a third clock signal (Clk3). As a result, one of the startup sequence modes is actually started, and thus the signal transmitting and receiving elements 120 transmit or receive signals according to the startup sequence mode.

In one embodiment, the first clock signal (clk1), the data signal (data), and the third clock signal (clk3) may be regarded as the control command transmitted by the user to the micro detection and treatment device 10 through the user operating device 150; for example, a doctor assigns and selects signal transmitting and receiving elements 120 of specific address parameters for the portion to be treated.

In one embodiment, the detailed structure may include at least one AND gate, wherein each AND gate is used to perform a logic operation on one of the address signals (S1~SN) and one of the startup signals (corresponding to one of the signal transmitting and receiving elements). In one embodiment, the quantity of the AND gates is equal to the product of the quantity of address signals (S1~SN) and the quantity of the startup signals.

As a result, the signal transmitting and receiving elements 120 may perform signal transmitting and receiving according to a specific startup sequence mode, so as to prevent the adjacent signal transmitting and receiving elements 120 from performing signal transmitting and receiving in the same period.

In one embodiment, each of the startup sequence sub-circuits 341~34N includes a plurality of flip-flops. In one embodiment, each startup sequence sub-circuit includes 32 flip-flops. In one embodiment, in order to achieve the i-th startup sequence mode (i.e., the signal transmitting and receiving elements 120 are started in a manner of spacing i signal transmitting and receiving elements 120), the key point is such that the output signal of the (i+1)-th flip of the i-th startup sequence sub-circuit 34i has to be coupled to the input end of the 1-st flip-flop, while the subsequent flip flops are applied in a similar manner, so as to achieve the i-th startup sequence mode, where i is a positive integer less than or equal to N. As a result, the startup sequence sub-circuits 341~34N may respectively implement the 1-st to N-th startup sequence modes.

With the biological object image-capturing and treatment system and method of the present invention, it is able to not only integrate the image-capturing function and the treatment function into the same micro detection and treatment device 10, but also greatly reduce the interference between adjacent signal channels through a startup sequence of special signal transmitting and receiving elements.

Figure 5:
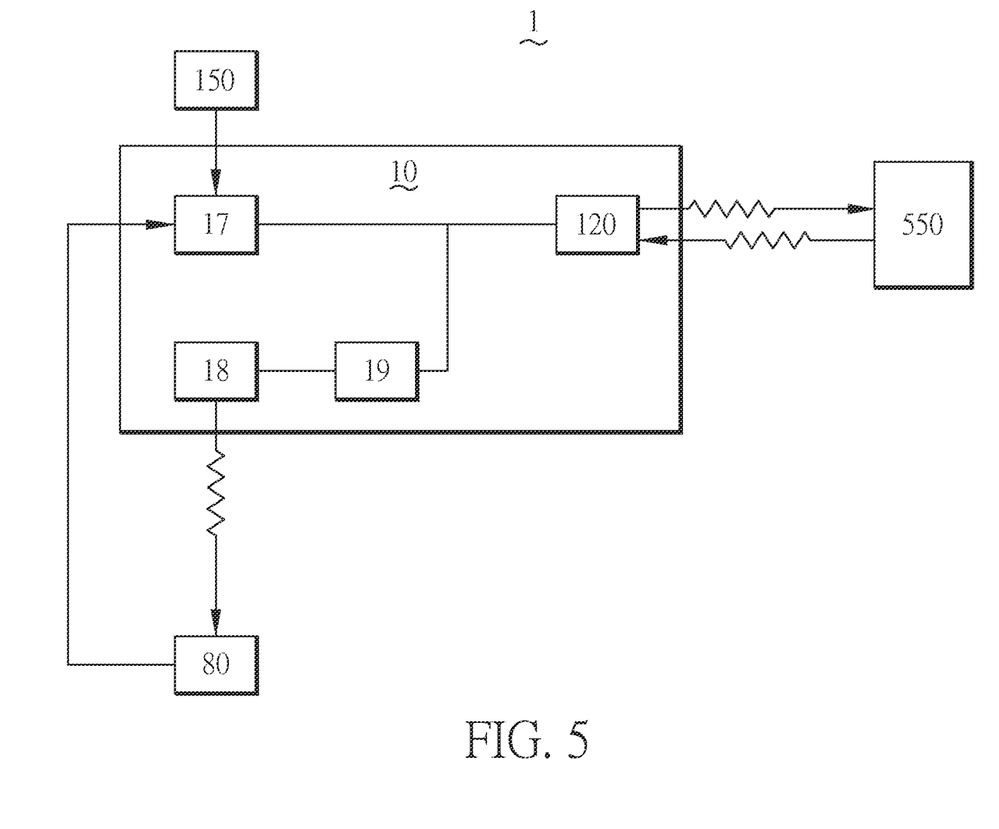
FIG. 5 is a schematic diagram illustrating the biological object image-capturing and treatment system according to another embodiment of the present invention.

Besides, the biological object image-capturing and treatment system 1 can be combined with an artificial intelligence (AI) model. FIG. 5 schematically illustrates the biological object image-capturing and treatment system 1 according to another embodiment of the present invention, and please refer to FIG. 1 to FIG. 4 at the same time. As shown in FIG. 5, the biological object image-capturing and treatment system 1 comprises the micro detection and treatment device 10, the user operating device 150, and an AI model 80. The micro detection and treatment device 10 comprises a plurality of signal transmitting and receiving elements 120, a transmitter 17, a receiver 18 and a transmitting/receiving switch 19.

The biological object image-capturing and treatment system 1 according to this embodiment may be used for executing the object stimulation procedure, wherein the transmitter 17 may control one of the signal transmitting and receiving elements 120 to transmit a stimulation signal to a particular target 550. The particular target 550 receives the stimulation signal and reflects a response signal. The receiver 18 may receive the response signal through one of the signal transmitting and receiving elements 120. The AI model 80 can perform machine learning.

Figure 6:
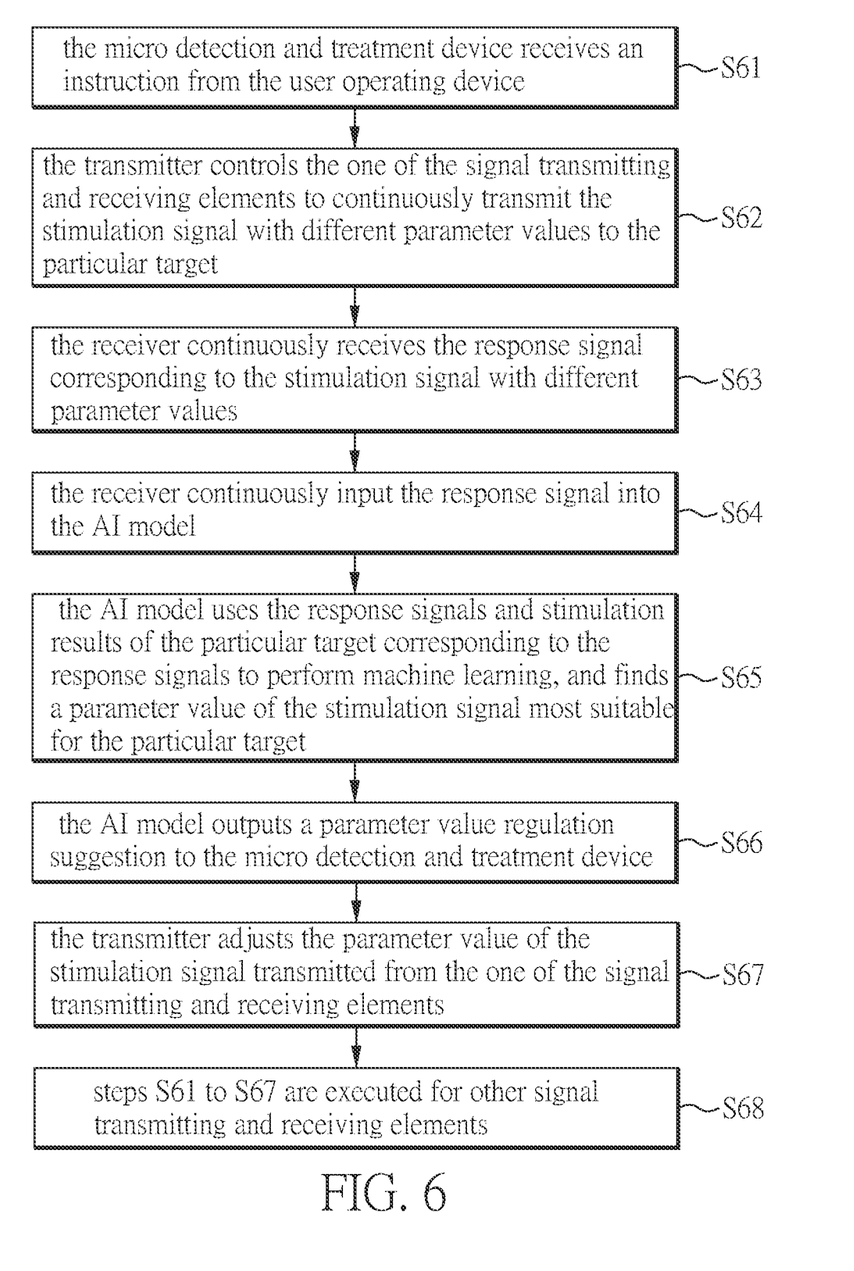
FIG. 6 is a flow chart illustrating the steps of the object stimulation procedure of the biological object image-capturing and treatment method according to an embodiment of the present invention.

FIG. 6 is a flow chart illustrating the steps of the object stimulation procedure of the biological object image-capturing and treatment method according to an embodiment of the present invention, and please refer to FIG. 5 at the same time.

As shown in FIG. 6, first, step S61 is executed, in which the micro detection and treatment device 10 receives an instruction from the user operating device 150. Then, step S62 is executed, in which the transmitter 170 selects one of the signal transmitting and receiving elements 120, and controls the one of the signal transmitting and receiving elements 120 to continuously transmit the stimulation signal with different parameter values to the particular target 550. Then, step S63 is executed, in which the receiver 18 continuously receives the response signal corresponding to the stimulation signal with different parameter values through one of the signal transmitting and receiving elements 120. Then, step S64 is executed, in which the receiver 18 continuously inputs the response signal into the AI model 80. Then, step S65 is executed, the AI model 80 uses the response signals and stimulation results of the particular target 550 corresponding to the response signals to perform machine learning, and finds a parameter value of the stimulation signal most suitable for the particular target 550 according to the result of the machine learning. Then, step S66 is executed, the AI model 80 outputs a parameter value regulation suggestion to the micro detection and treatment device 10 according to the parameter value of the stimulation signal most suitable for the particular target 550. Then, step S67 is executed, the transmitter 170 adjusts the parameter value of the stimulation signal transmitted from the one of the signal transmitting and receiving elements 120. Then, step S68 is executed, the processes of steps S61 to S67 are executed for other signal transmitting and receiving elements 120 until the parameter value of the stimulation signal transmitted from each of the signal transmitting and receiving elements 120 have been adjusted. Thus, the object stimulation procedure is completed. The sequence of the above steps can be changed as long as it is practicable.

It is noted that, in this embodiment, after the adjustment of the parameter value of the stimulation signal transmitted from a signal transmitting and receiving elements 120 is completed, the adjustment of the parameter value of the stimulation signal transmitted from another signal transmitting and receiving element 120 is performed. However, in other embodiments, as long as the hardware resource of the systems 1 is sufficient, the adjustment of the parameter value of the stimulation signal transmitted from the plurality of signal transmitting and receiving elements 120 may also be performed simultaneously, for example, a plurality of AI models 80 can be used for different signal transmitting and receiving elements 120.

Besides, although the response signals are used as input variables of the AI model 80 according to this embodiment, the stimulation signal with different parameter values can also be used as the input variables of the AI model 80 in other embodiment. In addition, the one of the signal transmitting and receiving elements 120 transmitting the stimulation signal and the one of the signal transmitting and receiving elements 120 receiving the response signal may be same or different signal transmitting and receiving elements 120.

Next, the details of each element will be described.

The signal transmitting and receiving elements 120 are applicable to the descriptions of the above embodiments. Besides, in the embodiment, each of the signal transmitting and receiving elements 120 corresponds to different particular target 550, for example, to different target objects 500 (shown in FIG. 1) or to different positions on the same target object 500.

In one embodiment, the transmitter 17 may be the controller 16 of the above embodiments, and has a signal generator 32 (as shown in FIG. 4).

In one embodiment, the receiver 18 may be a low voltage device with features of high performance and low noise, but it is not limited thereto.

In one embodiment, the transmitting/receiving switch 19 may be used to prevent the receiver 18 from receiving high voltage pulse from the controller 16, and to allow the receiver 18 to receive the low voltage pulse of the response signal through the signal transmitting and receiving element 120, thereby preventing the receiver 18 from being damaged by the high voltage pulse of the controller 16. In one embodiment, the voltage of the response signal is smaller than or equal to ±500 mV, but it is not limited thereto.

In one embodiment, the AI model 80 may be an artificial neural network. The AI model 80 may continuously perform deep learning according to the response signal corresponding to the stimulation signal with different parameter values (e.g. different power) and the stimulation results of the particular target 550 corresponding to each response signal, and find the parameter value of the stimulation signal most suitable for the particular target 550 according to the result of the deep learning, so as to generate the parameter value adjustment suggestion. In one embodiment, the response signal may indicate the amount of energy absorbed by the particular target 550, but it is not limited thereto.

In one embodiment, the type of the parameter value may be power, frequency or amplitude, and it is not limited thereto. For the convenience of explanation, power is used as an example in the following.

Furthermore, the object stimulation procedure may be performed inside a biological object or outside the biological object, as will be described separately below.

When the object stimulation procedure is performed inside the biological object, the micro detection and treatment device 10 is inserted into the biological object, and each of the signal transmitting and receiving elements 120 transmits stimulation signals to different positions of the target object 500, respectively, for example, each of the signal transmitting and receiving elements 120 corresponds to a position of the same organ, but it is not limited thereto.

When the object stimulation procedure is performed outside the biological object, the micro detection and treatment device 10 is inserted outside the biological object, and each of the signal transmitting and receiving elements 120 transmits stimulation signals to different particular targets 550, respectively, for example, one of the signal transmitting and receiving elements 120 can transmit the stimulation signal to an experimental sample, and another signal transmitting and receiving element 120 can transmit the stimulation signal to another experimental sample, but it is not limited thereto.

Besides, the first power signal of the image-capturing procedure or the second power signal of the treatment procedure according to the aforementioned embodiments can be adjusted by using the biological object image-capturing and treatment system 1 of FIG. 5 and the biological object image-capturing and treatment method of FIG. 6, wherein the AI model 80 can find a parameter value of the first power signal or the second power signal that is most suitable for the biological object or different positions of the biological object.

In this way, with the invention, it is able to automatically adjust power value of the stimulation signal transmitted by different signal transmitting and receiving elements 120 through the AI model 80, so as to provide power value most suitable for the particular target 550, thereby improving the stimulation effect.

Although the present invention has been explained in relation to its preferred embodiment, it is to be understood that many other possible modifications and variations can be made without departing from the spirit and scope of the invention as hereinafter claimed.

What is claimed is:

1. A biological object image-capturing and treatment system for performing an object stimulation procedure, comprising:

a micro detection and treatment device including a plurality of signal transmitting and receiving elements, wherein one of the signal transmitting and receiving elements continuously transmits a stimulation signal with different parameter values to a particular target, and one of the signal transmitting and receiving elements continuously receives response signal corresponding to the stimulation signal with different parameter values from the particular target; and an AI model using response signals corresponding to the stimulation signal with different parameter values from the particular target to perform machine learning, so as to output a parameter value adjustment suggestion to the micro detection and treatment device based on result of the machine learning, wherein the micro detection and treatment device adjusts the parameter value of the stimulation signal according to the parameter value adjustment suggestion, wherein a transmitter adjusts at least one of the parameter values of the stimulation signal transmitted from the one of the signal transmitting and receiving elements, wherein type of the at least one of the parameter values includes power, frequency and amplitude, wherein a diameter of each of the plurality of signal transmitting and receiving elements is equal to or smaller than 10000 micrometers, and the micro detection and treatment device is capable of being inserted into a human body;

wherein the biological object image-capturing and treatment system is further for a treatment procedure, and the treatment procedure comprises a first treatment mode and a second treatment mode, the first treatment mode is set to transmit a power signal to different positions of a target object by using one of the plurality of signal transmitting and receiving elements, the second treatment mode is set to transmit the power signal to the different positions of the target object by using at a part of the plurality of signal transmitting and receiving elements;

wherein the micro detection and treatment device further comprises a startup sequence setting module and a startup module, the startup sequence setting module controls the plurality of signal transmitting and receiving elements to perform one of a plurality of startup sequence modes for shifting transmitting timing and receiving timing of adjacent at least two elements of the plurality of signal transmitting and receiving elements, and the startup module generates a plurality of startup signals according to the startup sequence mode;

wherein, a detailed structure of the startup sequence setting module and the startup module comprises a signal generator, a shift register unit, and a latch data unit, wherein the shift register unit is coupled to the signal generator and comprises a plurality of startup sequence sub-circuits, wherein each of the startup sequence sub-circuits corresponds to a startup sequence mode of the plurality of startup sequence modes, and the latch data unit outputs a latch signal for performing an AND operation on the output of each of the startup sequence sub-circuits.

2. The biological object image-capturing and treatment system of claim 1, wherein the AI model is a deep learning model, and the stimulation signal is an ultrasonic signal.

3. The biological object image-capturing and treatment system of claim 1, wherein, the object stimulation procedure is performed in an biological object, the particular target is a particular position of a target object of the biological object, and each of the signal transmitting and receiving elements transmits a stimulation signal to different positions of the target object.

4. The biological object image-capturing and treatment system of claim 1, wherein, the object stimulation procedure is performed outside an biological object, the particular target is a target object, and each of the signal transmitting and receiving elements transmits a stimulation signal to different target objects.

5. A biological object image-capturing and treatment method performed by a biological object image-capturing and treatment system for performing an object stimulation procedure, wherein the system comprises a micro detection and treatment device and an AI model, and the micro detection and treatment device comprises a plurality of signal transmitting and receiving elements, the method comprising the steps of:

continuously transmitting a stimulation signal with different parameter values to a particular target by one of the signal transmitting and receiving elements;

continuously receiving response signal corresponding to the stimulation signal with different parameter values from the particular target by one of the signal transmitting and receiving elements;

using response signals corresponding to the stimulation signal with different parameter values to perform machine learning by the AI model, and outputting a parameter value adjustment suggestion based on result of the machine learning to the micro detection and treatment device by the AI model; and adjusting at least one of the parameter values of the stimulation signal based on the parameter value adjustment suggestion by the micro detection and treatment device, wherein a transmitter adjusts the at least one of the parameter values of the stimulation signal transmitted from the one of the signal transmitting and receiving elements, wherein type of the at least one of the parameter values includes power, frequency and amplitude, wherein a diameter of each of the plurality of signal transmitting and receiving elements is equal to or smaller than 10000 micrometers, and the micro detection and treatment device is for being inserted into a human body;

wherein the biological object image-capturing and treatment system is further for a treatment procedure, and the treatment procedure comprises a first treatment mode and a second treatment mode, the first treatment mode is set to transmit a power signal to different positions of a target object by using one of the plurality of signal transmitting and receiving elements, the second treatment mode is set to transmit the power signal to the different positions of the target object by using at a part of the plurality of signal transmitting and receiving elements;

wherein the micro detection and treatment device further comprises a startup sequence setting module and a startup module, the startup sequence setting module controls the plurality of signal transmitting and receiving elements to perform one of a plurality of startup sequence modes for shifting transmitting timing and receiving timing of adjacent at least two elements of the plurality of signal transmitting and receiving elements, and the startup module generates a plurality of startup signals according to the startup sequence mode;

wherein, a detailed structure of the startup sequence setting module and the startup module comprises a signal generator, a shift register unit, and a latch data unit, wherein the shift register unit is coupled to the signal generator and comprises a plurality of startup sequence sub-circuits, wherein each of the startup sequence sub-circuits corresponds to a startup sequence mode of the plurality of startup sequence modes, and the latch data unit outputs a latch signal for performing an AND operation on the output of each of the startup sequence sub-circuits.

6. The biological object image-capturing and treatment method of claim 5, wherein the AI model is a deep learning model, and the stimulation signal is an ultrasonic signal.

7. The biological object image-capturing and treatment method of claim 5, wherein, the object stimulation procedure is performed in an biological object, the particular target is a particular position of a target object of the biological object, and each of the signal transmitting and receiving elements transmits a stimulation signal to different positions of the target object.

8. The biological object image-capturing and treatment method of claim 5, wherein, the object stimulation procedure is performed outside a biological object, the particular target is a target object, and each of the signal transmitting and receiving elements transmits a stimulation signal to different target objects.

* * * * *